United States Patent
Shi et al.

(10) Patent No.: US 9,876,890 B2
(45) Date of Patent: Jan. 23, 2018

(54) AIR QUALITY MONITOR AND AIR QUALITY MONITORING SYSTEM CARRIED BY SMART PHONE

(71) Applicant: Shanghai Eawada Environmental Technology CO., Ltd, Shanghai (CN)

(72) Inventors: Shangxin Shi, Shanghai (CN); Yi Zhang, Shanghai (CN)

(73) Assignee: Shanghai Eawada Environmental Technology CO., Ltd, Shanghai (CN)

(*) Notice: Subject to any disclaimer, the term of this patent is extended or adjusted under 35 U.S.C. 154(b) by 0 days.

(21) Appl. No.: 15/645,946

(22) Filed: Jul. 10, 2017

(65) Prior Publication Data
US 2017/0310809 A1     Oct. 26, 2017

(30) Foreign Application Priority Data
Jan. 18, 2017  (CN) .......................... 2017 1 0037854

(51) Int. Cl.
*H04M 1/725*  (2006.01)
*G01N 33/00*  (2006.01)
*G01N 25/00*  (2006.01)

(52) U.S. Cl.
CPC ........ *H04M 1/72527* (2013.01); *G01N 25/00* (2013.01); *G01N 33/007* (2013.01); *G01N 33/0032* (2013.01); *G01N 33/0036* (2013.01)

(58) Field of Classification Search
CPC .......... H04M 1/72527; H04M 1/72533; G01N 25/00; G01N 33/0032; G01N 33/0036; G01N 33/007; G01N 27/74; G06Q 30/018; H01L 43/04; H01L 43/10; H01L 43/14
See application file for complete search history.

(56) References Cited

U.S. PATENT DOCUMENTS

| 2014/0292317 A1* | 10/2014 | Le Neel | ................. G01N 27/74 324/228 |
| 2016/0232536 A1* | 8/2016 | Couser | ................. G06Q 30/018 |
| 2017/0130981 A1* | 5/2017 | Willette | .................... F24F 3/16 |

\* cited by examiner

*Primary Examiner* — Thanh Le

(57) ABSTRACT

An air quality monitor carried by a smart phone and an air quality monitoring system carried by the smart phone are provided. The quality monitor carried by the smart phone includes a shell body, wherein a sensor is provided inside the shell body; a plug is provided on the shell body for being connected to the smart phone; a signal output terminal and a power input terminal of the sensor are both connected to the plug; wherein no power source or power source managing module is provided inside the shell body; no display module is provided on the shell body. Product weight and volume are greatly reduced, in such a manner that a product of the present invention is easy to carry. An air quality monitoring system carried by a smart phone includes: the smart phone, wherein the smart phone comprises a port and a signal processing system.

5 Claims, 1 Drawing Sheet

AIR QUALITY MONITOR AND AIR QUALITY MONITORING SYSTEM CARRIED BY SMART PHONE

CROSS REFERENCE OF RELATED APPLICATION

The present invention claims priority under 35 U.S.C. 119(a-d) to CN 201710037854.0, filed Jan. 24, 2017.

BACKGROUND OF THE PRESENT INVENTION

Field of Invention

The present invention relates to a field of quality controlling monitors, and more particularly to an air quality monitor.

Description of Related Arts

In addition to a sensor for obtaining monitoring parameters, the conventional quality controlling monitor further comprises a signal processing system for signal processing, and a battery for supplying power to the sensor and the signal processing system. As a result, volume and weight are relatively large, and it is very inconvenient to carry.

SUMMARY OF THE PRESENT INVENTION

An object of the present invention is to provide an air quality monitor carried by a smart phone, so as to overcome the above problem.

Another object of the present invention is to provide an air quality monitoring system carried by a smart phone Accordingly, in order to accomplish the above objects, the present invention provides:

an air quality monitor carried by a smart phone, comprising: a shell body, wherein a sensor is provided inside the shell body for obtaining air quality parameters; a plug is provided on the shell body for being connected to the smart phone; a signal output terminal and a power input terminal of the sensor are both connected to the plug;

wherein no power source or power source managing module is provided inside the shell body; no display module is provided on the shell body.

Innovation point 1: compared with conventional equipment, the present invention abandoned the battery, power management module, and display module, which can greatly reduce a product weight and volume, in such a manner that a product of the present invention is easy to carry.

Innovation point 2: with modular designs, different air quality parameters can be monitored by selecting different products.

Innovation point 3: the product of the present invention uses the smart phone as a carrier, wherein the sensor is supply by the power of the smart phone through the plug, and the air quality parameters obtained is analyzed and processed with the help of the signal processing system of the smart phone; or, the air quality parameters obtained are sent to the cloud-end where analyzing and processing happen. The present invention is conducive to reduction of the volume and the weight, and more critical, enables large data processing and analysis through the cloud-end.

These and other objectives, features, and advantages of the present invention will become apparent from the following detailed description, the accompanying drawings, and the appended claims.

DETAILED DESCRIPTION OF THE PREFERRED EMBODIMENT

Figure 1:
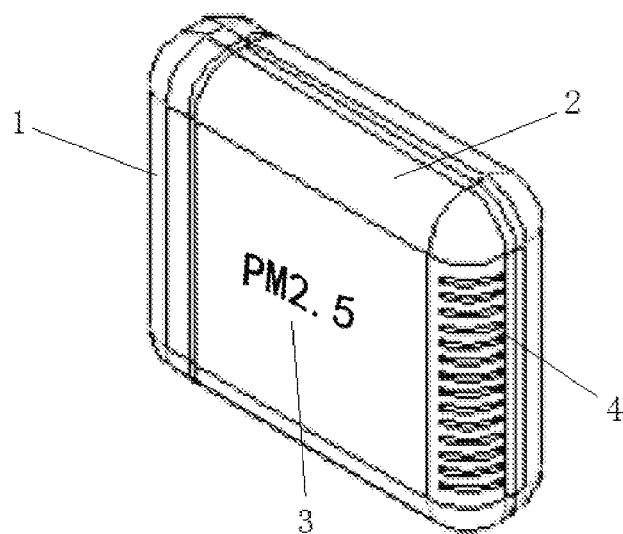
FIG. 1 is a partial structure view of an air quality monitor carried by a smart phone.

Referring to the drawings, the present invention is further illustrated as follows.

Figure 2:
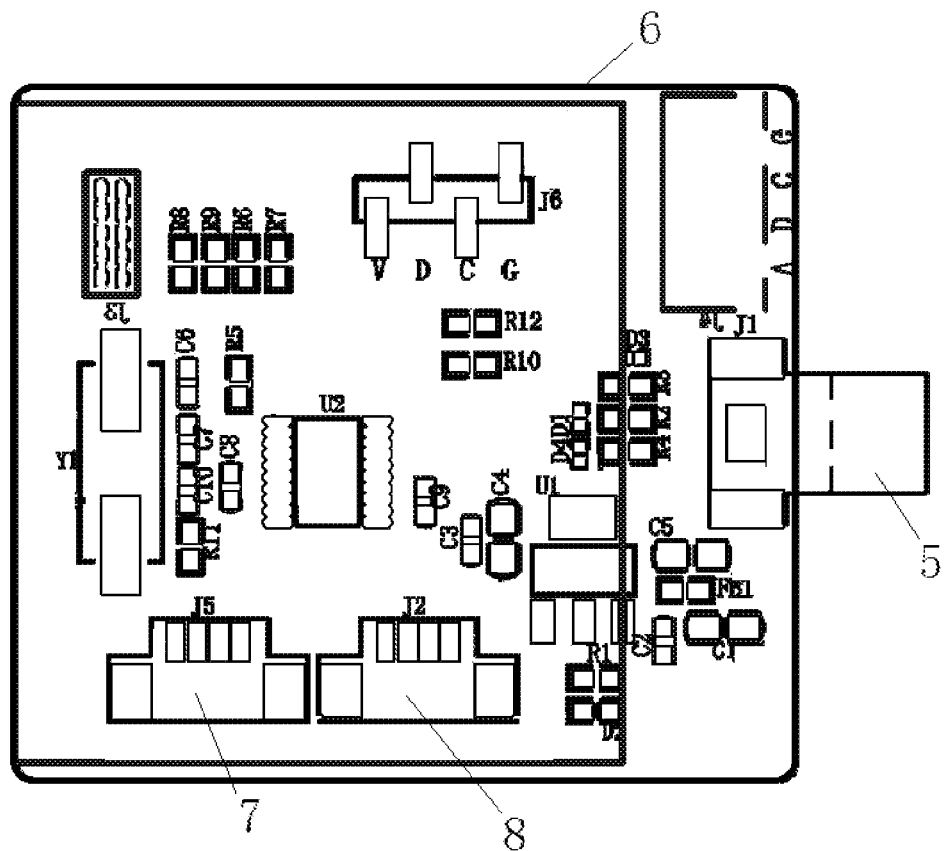
FIG. 2 is a partial structure view thereof.

Referring to FIGS. 1-2, an air quality monitor carried by a smart phone is illustrated, comprising: a shell body 2, wherein a sensor is provided inside the shell body 2 for obtaining air quality parameters; a plug 5 is provided on the shell body 2 for being connected to the smart phone; a signal output terminal and a power input terminal of the sensor are both connected to the plug 5; wherein no power source or power source managing module is provided inside the shell body 2; no display module is provided on the shell body 2.

A signal processing circuit is also provided inside the shell body 2, and the sensor is connected to the signal processing circuit; the signal processing circuit is connected to the plug 5 through an OTG (On-The-Go) module. The OTG module obtains power from the smart phone, and communicates data with the smart phone having an OTG function, in such a manner that the smart phone having the OTG function obtains the data of the sensor.

Innovation point 1: compared with conventional equipment, the present invention abandoned the battery, power management module, and display module, which can greatly reduce a product weight and volume, in such a manner that a product of the present invention is easy to carry.

Innovation point 2: with modular designs, different air quality parameters can be monitored by selecting different products.

Innovation point 3: the product of the present invention uses the smart phone as a carrier, wherein the sensor is supply by the power of the smart phone through the plug, and the air quality parameters obtained is analyzed and processed with the help of the signal processing system of the smart phone; or, the air quality parameters obtained are sent to the cloud-end where analyzing and processing happen. The present invention is conducive to reduction of the volume and the weight, and more critical, enables large data processing and analysis through the cloud-end.

A USB (universal serial bus) hub module is connected to the OTG module inside the shell body 2; the USB hub module has a USB port arranged on the shell body 2, and the USB port comprises an external interface on the shell body;

wherein through the external interface of the USB port, another air quality monitor carried by the smart phone is connected, in such a manner that devices with different functions are connected to the same smart phone, so as to synchronically monitor with different sensors.

Preferably, the interface is provided at a bottom portion of the shell body 2, and the plug 5 is provided at a top portion of the shell body 2, in such a manner that the shell body 2 will not be a blockage when the plug 2 and the interface are respectively connected. Alternatively, the interface is provided at a side wall of the shell body 2, and the plug 5 is provided at the top portion of the shell body 2, in such a manner that the shell body 2 will not be the blockage when the plug 2 and the interface are respectively connected. The shell body 2 may have two interfaces at both sides.

The plug 5 is preferably a USB Type-C plug, and an adapter is a USB Type-C to Apple Lightning adapter. The USB Type-C plug is able to power transmission as well as signal transmission. Therefore, there is no need to modify the plug. As the USB Type-C interfaces are used by more and more mobile phones, the air quality monitor using the USB Type-C plug will be universal. No doubt, the plug 5 may be a USB plug, a mini USB plug and so on. The interface is preferably a Micro USB interface.

The air quality monitor carried by the smart phone further comprises a lid 1, wherein the lid 1 is detachably buckled at one end of the shell body 2 where the plug 1 is. Meanwhile, the plug 5 is inserted into the lid 1 to protect the plug 5, avoiding plug damage. A container is provided on the lid 1 for containing the adapter, and at least one adapter is placed in the container, in case the plug 5 mismatches with phone ports. When mismatching, the plug 5 may be connected to the smart phone through the adapter. The shell body 2 comprises an upper shell and a lower shell 6 buckled together. The plug 5 is preferably arranged on the lower shell 6, a text marking 3 about monitor target of the sensor (such as temperature, humidity, PM2.5, formaldehyde and $CO_2$) is concavely engraved on a top surface of the upper shell, and the sensor inside the shell body 2 corresponds to the text marking, so as to identify a type of the air quality monitor. For example, if a temperature sensor is inside the shell body 2, then "temperature" is concavely engraved on the top surface; if a humidity sensor is inside the shell body 2, then "humidity" is concavely engraved on the top surface; if a PM2.5 sensor is inside the shell body 2, then "PM2.5" is concavely engraved on the top surface; if a formaldehyde sensor is inside the shell body 2, then "formaldehyde" is concavely engraved on the top surface; if a $CO_2$ sensor is inside the shell body 2, then "$CO_2$" is concavely engraved on the top surface. The shell body 2 is buckled with the lid 1 and forms a cubic structure, with a width of 21 mm±5 mm, a length of 71 mm±5 mm, and a height of 63 mm±5 mm. A total weight of the air quality monitor carried by the smart phone is no more than 70 g.

There may be only on sensor inside the shell body 2, which is a temperature sensor, a humidity sensor, a PM2.5 sensor, a formaldehyde sensor, or a $CO_2$ sensor. There may be two sensors inside the shell body 2, and the two sensors are any two selected from a temperature sensor, a humidity sensor, a PM2.5 sensor, a formaldehyde sensor, and a $CO_2$ sensor;

wherein two or more than two of the sensors are respectively connected to the signal processing circuit; the processing circuit is connected to the plug 5 through the OTG module; the OTG module obtains the power from the smart phone, and communicates the data with the smart phone having the OTG function, in such a manner that the smart phone having the OTG function obtains the data of the sensors.

When the sensor inside the shell body 2 is the PM2.5 sensor, the formaldehyde sensor, or the $CO_2$ sensor, a vent 4 is drilled on the shell body 2 in such a manner that the sensitive element communicates with air to be monitored. As a result, the air to be monitored reaches the sensitive element, ensuring accuracy of monitoring.

Preferably, both the formaldehyde sensor and the PM2.5 sensor are arranged inside the shell body 2, and the vent 4 is drilled on the side wall of the shell body 2, wherein the formaldehyde sensor and the PM2.5 sensor are arranged behind the vent 4.

The air quality monitor carried by the smart phone further comprises a sensor sensitivity enhancement system; wherein the sensor sensitivity enhancement system comprises a gas chamber on the shell body 2, wherein a sensor sensitive element is provided inside the gas chamber;

wherein an openable sealing door is provided at a gas input of the gas chamber; an electric heater is also provided inside the gas chamber for improving activities of air compositions or providing reaction effects by heating, so as to increase sensitivity of monitoring;

wherein a temperature sensor is also provided inside the gas chamber, so as to provide real-time temperature parameters, in such a manner that the sensor sensitivity enhancement system modifies monitored values based on temperatures, which increases accuracy of monitoring.

The sealing door adapts an electric mechanism, or a rubber stopper.

Two sensor sensitive elements are provided inside the gas chamber, respectively the formaldehyde sensor and the PM2.5 sensor.

The sensor sensitivity enhancement system further comprises a piston mechanism, wherein a gas outlet of the piston mechanism communicates with the gas chamber;

wherein the piston mechanism adapts a motor as a driving mechanism, a power source terminal of the motor is connected to the signal processing circuit, so as to obtain the power from the smart phone through the OTG module;

wherein gas inside the gas chamber is compressed by the piston mechanism for increasing density, so as to increase the accuracy of monitoring;

wherein a blower is also provided inside the gas chamber for driving the gas inside the gas chamber to flow; a power input terminal of the blower is connected to the signal processing circuit, so as to obtain the power from the smart phone through the OTG module;

wherein the gas inside the gas chamber is driven to flow by the blower, in such a manner that reacted gas rapidly flows away from a sensitive surface of the sensor sensitive element, and unreacted gas contacts with the sensitive surface, so as to improve the sensitivity.

Especially, accuracy of the formaldehyde sensor and the PM2.5 sensor is improved.

The gas chamber is provided on the shell body 2 with an opening facing outwards, wherein the sensor sensitive element is provided inside the gas chamber.

The gas chamber is preferably provided at the side wall of the shell body 2 rather than upper or lower wall of the shell body 2. As a result, the shell body 2 is flat and inner space thereof is fully used, in such a manner that the shell body 2 won't be too large. In addition, air can enter the gas chamber when shaking the shell body 2 with hands. According to long-term observation by the applicant, humans are used to shaking phones in a left-right direction rather than an up-down direction or a front-rear direction. Preferably, formaldehyde sensor sensitive element 7 and a PM2.5 sensor sensitive element 8 are both provided in the gas chamber from left to right, so as to avoid a large thickness when arranging from up to down.

Two supporting poles are arranged inside the gas chamber, wherein the formaldehyde sensor sensitive element 7 and the PM2.5 sensor sensitive element 8 are both cylindrical and sleeved on the supporting poles respectively. The present invention optimizes a structure of the sensor sensitive element. Compared with a plate structure, present invention has a small volume. More importantly, the present invention increases a contact area with air, leading to improvement of monitoring signal accuracy.

Preferably, the supporting poles are hollow supporting poles. One end of the supporting pole is connected to a bottom of the gas chamber, and the other end has an opening. The opening communicates with the vent 4, so as to take advantage of a hollow structure of the supporting pole. As a result, air contacts with the sensor sensitive element from an internal side, which further improves the contact area therebetween, and is conducive to improving accuracy of monitoring.

The openable sealing door is provided at the opening of the gas chamber. After opening the sealing door, air enters; after closing the sealing door, the sensor in the gas chamber is protected. More importantly, a space between the sealing door and the gas chamber is used for sampling and storing air. The blower cooperates with the sealing door through a switch. When the sealing door is opened, the blower starts; when the sealing door is closed, the blower ends. The switch is an inches switch or a photosensitive element. When the switch is the photosensitive element, the sealing door is light-proof. The blower is preferably arranged on a side wall of the gas chamber, and the sensor sensitive element is preferably arranged at a bottom of the gas chamber to avoid being blown by the blower, so as to ensure that air contacts with the sensor sensitive element. Preferably, a distance between the blower and the sensor sensitive element is no less than 5 mm, so as to ensure enough air at the sensor sensitive element.

The plug 5 is able to slide up and down. By sliding the plug 5, a relative position of the shell body 2 and the smart phone is adjustable. During monitoring, the shell body 2 and the smart phone can both be laid down. On one hand, plug damage is avoided. On the other hand, vibration during monitoring, which will affect accuracy, is prevented.

An air quality monitoring system carried by a smart phone is illustrated, comprising: the smart phone, wherein the smart phone comprises a port and a signal processing system, wherein the signal processing system is connected to the port; the air quality monitoring system further comprises an air quality monitor carried by the smart phone, wherein a plug of the air quality monitor carried by the smart phone is inserted into the port.

A program processing sensor signals is run on the smart phone, and the signal processing system is a system capable of processing the sensor signals; the smart phone runs the program for analyzing a monitored air quality; a displayer is provided on the smart phone and is connected to the signal processing system; the smart phone displays analysis results through the displayer; wherein the smart phone sends the signals to a cloud-end server through a communication module which is connected to a signal processing module.

A connecting sleeve made of an elastic material is provided between the smart phone and the air quality monitor carried by the smart phone; one end of the connecting sleeve is sleeved on the smart phone, and the other end of the connecting sleeve is sleeved on the air quality monitor carried by the smart phone. As a result, the air quality monitor well contacts with the smart phone, which avoids inaccurate monitoring result caused by weak signals. More importantly, after connected through the connecting sleeve, the air quality monitor and the smart phone are used as an individual sensor for replacing conventional sensors. Generally, all smart phones have sensor processing abilities. Therefore, with the present invention, uses can take advantage of old smart phones and conveniently assemble a sensor, so as to rapidly and cheaply establish an intelligent home furnishing system.

An isolating plate is provided in the connecting sleeve, and an adapter is provided on the isolating plate, wherein the air quality monitor carried by the smart phone is connected to one end of the adapter, and the smart is connected to the other end of the adapter, so as to be conveniently connected together. The connecting sleeve covers at least ⅓ area of the air quality monitor carried by the smart phone. The connecting sleeve is preferably a silicon sleeve.

The air quality monitor carried by the smart phone is adapted, comprising:

a shell body, wherein a sensor is provided inside the shell body for obtaining air quality parameters; a plug is provided on the shell body for being connected to the smart phone; a signal output terminal and a power input terminal of the sensor are both connected to the plug;

wherein no power source or poser source managing module is provided inside the shell body; no display module is provided on the shell body;

wherein a signal processing circuit is also provided inside the shell body, and the sensor is connected to the signal processing circuit; the signal processing circuit is connected to the plug through an OTG (On-The-Go) module;

wherein the OTG module obtains power from the smart phone, and communicates data with the smart phone having an OTG function, in such a manner that the smart phone having the OTG function obtains the data of the sensor;

wherein a USB (universal serial bus) hub module is connected to the OTG module inside the shell body; the USB hub module has a USB port arranged on the shell body, and the USB port comprises an external interface on the shell body;

wherein through the external interface of the USB port, another air quality monitor carried by the smart phone is connected, in such a manner that devices with different functions are connected to the same smart phone, so as to synchronically monitor with different sensors;

wherein the air quality monitor further comprising a sensor sensitivity enhancement system;

wherein the sensor sensitivity enhancement system comprises a gas chamber, wherein a sensor sensitive element is provided inside the gas chamber;

wherein an openable sealing door is provided at a gas input of the gas chamber; an electric heater is also provided inside the gas chamber for improving activities of air compositions or providing reaction effects by heating, so as to increase sensitivity of monitoring;

wherein a temperature sensor is also provided inside the gas chamber, so as to provide real-time temperature parameters, in such a manner that the sensor sensitivity enhancement system modifies monitored values based on temperatures, which increases accuracy of monitoring;

wherein the sensor sensitivity enhancement system further comprises a piston mechanism, wherein a gas outlet of the piston mechanism communicates with the gas chamber;

wherein the piston mechanism adapts a motor as a driving mechanism, a power source terminal of the motor is connected to the signal processing circuit, so as to obtain the power from the smart phone through the OTG module;

wherein gas inside the gas chamber is compressed by the piston mechanism for increasing density, so as to increase the accuracy of monitoring;

wherein a blower is also provided inside the gas chamber for driving the gas inside the gas chamber to flow; a power input terminal of the blower is connected to the signal processing circuit, so as to obtain the power from the smart phone through the OTG module;

wherein the gas inside the gas chamber is driven to flow by the blower, in such a manner that reacted gas rapidly flows away from a sensitive surface of the sensor sensitive element, and unreacted gas contacts with the sensitive surface, so as to improve the sensitivity.

One skilled in the art will understand that the embodiment of the present invention as shown in the drawings and described above is exemplary only and not intended to be limiting. It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An air quality monitor carried by a smart phone, comprising: a shell body, wherein a sensor is provided inside the shell body for obtaining air quality parameters; a plug is provided on the shell body for being connected to the smart phone; a signal output terminal and a power input terminal of the sensor are both connected to the plug;

wherein no power source or power source managing module is provided inside the shell body; no display module is provided on the shell body;

wherein a signal processing circuit is also provided inside the shell body, and the sensor is connected to the signal processing circuit; the signal processing circuit is connected to the plug through an OTG (On-The-Go) module;

wherein the OTG module obtains power from the smart phone, and communicates data with the smart phone having an OTG function, in such a manner that the smart phone having the OTG function obtains the data of the sensor;

wherein a USB (universal serial bus) hub module is connected to the OTG module inside the shell body; the USB hub module has a USB port arranged on the shell body, and the USB port comprises an external interface on the shell body;

wherein through the external interface of the USB port, another air quality monitor carried by the smart phone is connected, in such a manner that devices with different functions are connected to the same smart phone, so as to synchronically monitor with different sensors;

wherein two sensors are provided inside the shell body, and the two sensors are any two selected from a temperature sensor, a humidity sensor, a PM2.5 sensor, a formaldehyde sensor, and a $CO_2$ sensor;

wherein two or more than two of the sensors are respectively connected to the signal processing circuit; the processing circuit is connected to the plug through the OTG module; the OTG module obtains the power from the smart phone, and communicates the data with the smart phone having the OTG function, in such a manner that the smart phone having the OTG function obtains the data of the sensors.

2. The air quality monitor carried by the smart phone, as recited in claim 1, further comprising a sensor sensitivity enhancement system;

wherein the sensor sensitivity enhancement system comprises a gas chamber on the shell body, wherein a sensor sensitive element is provided inside the gas chamber;

wherein an openable sealing door is provided at a gas input of the gas chamber; an electric heater is also provided inside the gas chamber for improving activities of air compositions or providing reaction effects by heating, so as to increase sensitivity of monitoring;

wherein a temperature sensor is also provided inside the gas chamber, so as to provide real-time temperature parameters, in such a manner that the sensor sensitivity enhancement system modifies monitored values based on temperatures, which increases accuracy of monitoring;

wherein the sensor sensitivity enhancement system further comprises a piston mechanism, wherein a gas outlet of the piston mechanism communicates with the gas chamber;

wherein the piston mechanism adapts a motor as a driving mechanism, a power source terminal of the motor is connected to the signal processing circuit, so as to obtain the power from the smart phone through the OTG module;

wherein gas inside the gas chamber is compressed by the piston mechanism for increasing density, so as to increase the accuracy of monitoring;

wherein a blower is also provided inside the gas chamber for driving the gas inside the gas chamber to flow; a power input terminal of the blower is connected to the signal processing circuit, so as to obtain the power from the smart phone through the OTG module;

wherein the gas inside the gas chamber is driven to flow by the blower, in such a manner that reacted gas rapidly flows away from a sensitive surface of the sensor sensitive element, and unreacted gas contacts with the sensitive surface, so as to improve the sensitivity.

3. An air quality monitoring system carried by a smart phone, comprising: the smart phone, wherein the smart phone comprises a port and a signal processing system, wherein the signal processing system is connected to the port; the air quality monitoring system further comprises an air quality monitor carried by the smart phone, wherein a plug of the air quality monitor carried by the smart phone is inserted into the port;

wherein the air quality monitor carried by the smart phone comprises:

a shell body, wherein a sensor is provided inside the shell body for obtaining air quality parameters; a plug is provided on the shell body for being connected to the smart phone; a signal output terminal and a power input terminal of the sensor are both connected to the plug;

wherein no power source or poser source managing module is provided inside the shell body; no display module is provided on the shell body;

wherein a signal processing circuit is also provided inside the shell body, and the sensor is connected to the signal processing circuit; the signal processing circuit is connected to the plug through an OTG (On-The-Go) module;

wherein the OTG module obtains power from the smart phone, and communicates data with the smart phone having an OTG function, in such a manner that the smart phone having the OTG function obtains the data of the sensor;

wherein a USB (universal serial bus) hub module is connected to the OTG module inside the shell body; the USB hub module has a USB port arranged on the shell body, and the USB port comprises an external interface on the shell body;

wherein through the external interface of the USB port, another air quality monitor carried by the smart phone is connected, in such a manner that devices with different functions are connected to the same smart phone, so as to synchronically monitor with different sensors;

wherein the air quality monitor further comprising a sensor sensitivity enhancement system;

wherein the sensor sensitivity enhancement system comprises a gas chamber, wherein a sensor sensitive element is provided inside the gas chamber;

wherein an openable sealing door is provided at a gas input of the gas chamber; an electric heater is also provided inside the gas chamber for improving activities of air compositions or providing reaction effects by heating, so as to increase sensitivity of monitoring;

wherein a temperature sensor is also provided inside the gas chamber, so as to provide real-time temperature parameters, in such a manner that the sensor sensitivity enhancement system modifies monitored values based on temperatures, which increases accuracy of monitoring;

wherein the sensor sensitivity enhancement system further comprises a piston mechanism, wherein a gas outlet of the piston mechanism communicates with the gas chamber;

wherein the piston mechanism adapts a motor as a driving mechanism, a power source terminal of the motor is connected to the signal processing circuit, so as to obtain the power from the smart phone through the OTG module;

wherein gas inside the gas chamber is compressed by the piston mechanism for increasing density, so as to increase the accuracy of monitoring;

wherein a blower is also provided inside the gas chamber for driving the gas inside the gas chamber to flow; a power input terminal of the blower is connected to the signal processing circuit, so as to obtain the power from the smart phone through the OTG module;

wherein the gas inside the gas chamber is driven to flow by the blower, in such a manner that reacted gas rapidly flows away from a sensitive surface of the sensor sensitive element, and unreacted gas contacts with the sensitive surface, so as to improve the sensitivity.

4. The air quality monitoring system carried by the smart phone, as recited by claim 3, wherein a program processing sensor signals is run on the smart phone, and the signal processing system is a system capable of processing the sensor signals; the smart phone runs the program for analyzing a monitored air quality; a displayer is provided on the smart phone and is connected to the signal processing system; the smart phone displays analysis results through the displayer;

wherein the smart phone sends the signals to a cloud-end server through a communication module which is connected to a signal processing module.

5. The air quality monitoring system carried by the smart phone, as recited by claim 3, wherein:

a connecting sleeve made of an elastic material is provided between the smart phone and the air quality monitor carried by the smart phone; one end of the connecting sleeve is sleeved on the smart phone, and the other end of the connecting sleeve is sleeved on the air quality monitor carried by the smart phone.

* * * * *